United States Patent
Takahashi

(10) Patent No.: US 12,048,592 B2
(45) Date of Patent: Jul. 30, 2024

(54) THREE-DIMENSIONAL ULTRASOUND IMAGING SUPPORT APPARATUS, THREE-DIMENSIONAL ULTRASOUND IMAGING SUPPORT METHOD, AND THREE-DIMENSIONAL ULTRASOUND IMAGING SUPPORT PROGRAM

(71) Applicant: FUJIFILM Corporation, Tokyo (JP)

(72) Inventor: Azuma Takahashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 412 days.

(21) Appl. No.: 17/541,250

(22) Filed: Dec. 3, 2021

(65) Prior Publication Data
US 2022/0087652 A1 Mar. 24, 2022

Related U.S. Application Data
(63) Continuation of application No. PCT/JP2020/019903, filed on May 20, 2020.

(30) Foreign Application Priority Data
Jun. 6, 2019 (JP) .................................. 2019-106448

(51) Int. Cl.
*A61B 8/08* (2006.01)
*A61B 8/00* (2006.01)
(Continued)

(52) U.S. Cl.
CPC .............. *A61B 8/5246* (2013.01); *A61B 8/14* (2013.01); *A61B 8/4254* (2013.01);
(Continued)

(58) Field of Classification Search
CPC .............. A61B 8/08; A61B 8/14; A61B 8/483; A61B 8/4254; A61B 8/4263;
(Continued)

(56) References Cited

U.S. PATENT DOCUMENTS

| 2013/0225986 A1 | 8/2013 | Eggers et al. |
| 2016/0270757 A1 | 9/2016 | Toma et al. |

(Continued)

FOREIGN PATENT DOCUMENTS

| JP | 2014528347 | 10/2014 |
| JP | 2016506781 | 3/2016 |

(Continued)

OTHER PUBLICATIONS

"International Search Report (Form PCT/ISA/210) of PCT/JP2020/019903," mailed on Jul. 7, 2020, with English translation thereof, pp. 1-5.

(Continued)

*Primary Examiner* — Boniface N Nganga
(74) *Attorney, Agent, or Firm* — JCIPRNET

(57) ABSTRACT

A three-dimensional ultrasound imaging support apparatus includes: a processor configured to generate a three-dimensional ultrasound image based on a plurality of two-dimensional ultrasound images which are imaged by an ultrasound probe at different positions of a certain portion of a subject and an imaging position of the ultrasound probe for each imaging; estimate an imaging portion corresponding to the two-dimensional ultrasound image and to the three-dimensional ultrasound image; determine, by using a guideline in which a plurality of imaging targets to be imaged are defined in advance for each portion of the subject, for the estimated imaging portion, whether or not all of the plurality of imaging targets defined in advance in the guideline are imaged; and perform notification indicating that the imaging target which is not imaged is present in a case where it is determined that the imaging target which is not imaged is present.

11 Claims, 10 Drawing Sheets

(51) Int. Cl.
*A61B 8/14* (2006.01)
*G06T 7/00* (2017.01)
*G06T 7/73* (2017.01)
*G16H 30/40* (2018.01)

(52) U.S. Cl.
CPC .......... *A61B 8/4263* (2013.01); *G06T 7/0012* (2013.01); *G06T 7/73* (2017.01); *G16H 30/40* (2018.01); *G06T 2207/10136* (2013.01); *G06T 2207/30168* (2013.01); *G06T 2207/30204* (2013.01)

(58) Field of Classification Search
CPC ....... A61B 8/5246; G06T 7/0012; G06T 7/73; G06T 2207/10136; G06T 2207/30168; G06T 2207/30204; G16H 30/40
See application file for complete search history.

(56) References Cited

U.S. PATENT DOCUMENTS

| | | |
|---|---|---|
| 2017/0128045 A1 | 5/2017 | Roundhill et al. |
| 2018/0132722 A1 | 5/2018 | Eggers et al. |
| 2018/0150598 A1 | 5/2018 | Kohls et al. |
| 2018/0325488 A1 | 11/2018 | Zhu et al. |

FOREIGN PATENT DOCUMENTS

| | | |
|---|---|---|
| JP | 2017519579 | 7/2017 |
| JP | 6323335 | 5/2018 |
| WO | 2014113530 | 7/2014 |
| WO | 2017094577 | 6/2017 |

OTHER PUBLICATIONS

"Written Opinion of the International Searching Authority (Form PCT/ISA/237)" of PCT/ JP2020/019903, mailed on Jul. 7, 2020, with English translation thereof, pp. 1-8.

THREE-DIMENSIONAL ULTRASOUND IMAGING SUPPORT APPARATUS, THREE-DIMENSIONAL ULTRASOUND IMAGING SUPPORT METHOD, AND THREE-DIMENSIONAL ULTRASOUND IMAGING SUPPORT PROGRAM

CROSS-REFERENCE TO RELATED APPLICATIONS

This application is a Continuation of PCT International Application No. PCT/JP2020/019903 filed on May 20, 2020, which claims priority under 35 U.S.C § 119(a) to Japanese Patent Application No. 2019-106448 filed on Jun. 6, 2019. Each of the above application(s) is hereby expressly incorporated by reference, in its entirety, into the present application.

BACKGROUND OF THE INVENTION

1. Field of the Invention

The present disclosure relates to a three-dimensional ultrasound imaging support apparatus, a three-dimensional ultrasound imaging support method, and a three-dimensional ultrasound imaging support program capable of supporting imaging of an ultrasound image by a three-dimensional ultrasound apparatus that generates a three-dimensional ultrasound image.

2. Description of the Related Art

In recent years, with advancements in medical apparatuses such as a computed tomography (CT) apparatus, a magnetic resonance imaging (MRI) apparatus, and an ultrasound diagnosis apparatus, image diagnosis using higher quality and higher resolution medical images has become possible. In the ultrasound diagnosis apparatus, there is known a technique of generating a three-dimensional ultrasound image from two-dimensional ultrasound images which are acquired by performing imaging by an ultrasound probe and imaging positions of the ultrasound probe. In this technique, in order to generate a high-resolution three-dimensional ultrasound image, it is necessary to densely image a plurality of two-dimensional ultrasound images for a target portion of a subject. However, a body surface of the subject has irregularities, and as a result, it is difficult to uniformly and densely image a plurality of two-dimensional ultrasound images. JP2014-528347A discloses a technique of warning an operator of the ultrasound probe in a case where a distance between the images captured by the ultrasound probe exceeds a maximum distance. In addition, JP2016-506781A discloses a technique of superimposing and displaying a path in which imaging is to be performed again on an image of a target portion in a case where a distance between images, a speed of an ultrasound probe, or the like is excessive. Further, JP6323335B discloses a technique of navigating a movement of an ultrasound probe to an imaging target location of a subject.

SUMMARY OF THE INVENTION

On the other hand, in ultrasound diagnosis, for each portion of a subject, a guideline in which examination methods for each portion are defined in detail is provided. For example, in a case where an imaging portion is a carotid artery, it is defined that a tomographic image is observed in two directions of a minor-axis cross section direction of a blood vessel and a major-axis cross section direction of a blood vessel, and it is defined that observation regions include a common carotid artery, a carotid sinus, an internal carotid artery, and a vertebral artery as regions which can be observed on both right and left sides. Further, it is also defined that observation regions include an external carotid artery, a subclavian artery, a brachiocephalic artery, a superficial temporal artery, and a branch artery of the arteries, as necessary. As described above, in the guideline, imaging targets to be imaged, such as a common carotid artery and a carotid sinus in the observation region, are defined for each portion of the subject, such as a carotid artery.

The techniques described in JP2014-528347A, JP2016-506781A, and JP6323335B do not disclose a method of determining whether or not a plurality of imaging targets to be imaged that are defined in the guideline are imaged for each portion of the subject. For this reason, in order to image all of the plurality of imaging targets to be imaged that are defined in the guideline for each portion of the subject, a user needs to operate the ultrasound probe while checking the guideline for each imaging portion. As a result, it takes time and effort. Further, in a case where it is necessary to perform imaging many times, a user may forget imaging of imaging targets to be imaged.

The present disclosure has been made in view of the above circumstances, and an object of the present disclosure is to allow a user to easily confirm whether or not all of the imaging targets conforming to the guideline are imaged.

According to an aspect of the present disclosure, there is provided a three-dimensional ultrasound imaging support apparatus that supports imaging of an ultrasound image by a three-dimensional ultrasound apparatus for generating a three-dimensional ultrasound image, the three-dimensional ultrasound imaging support apparatus including: an image acquisition unit that acquires a plurality of two-dimensional ultrasound images which are imaged by an ultrasound probe at different positions of a certain portion among a plurality of portions of a subject; an imaging position acquisition unit that acquires an imaging position of the ultrasound probe for each imaging; a three-dimensional ultrasound image generation unit that generates a three-dimensional ultrasound image based on the plurality of two-dimensional ultrasound images which are acquired by the image acquisition unit and the imaging position for each imaging which is acquired by the imaging position acquisition unit; an estimation unit that estimates, from the plurality of portions of the subject, an imaging portion corresponding to the two-dimensional ultrasound image and to the three-dimensional ultrasound image, based on at least one of the two-dimensional ultrasound image acquired by the image acquisition unit or the three-dimensional ultrasound image generated by the three-dimensional ultrasound image generation unit; a determination unit that determines, by using a guideline in which a plurality of imaging targets to be imaged are defined in advance for each of the portions of the subject, for the imaging portion estimated by the estimation unit, whether or not all of the plurality of imaging targets are imaged in at least one of the plurality of two-dimensional ultrasound images or the three-dimensional ultrasound image, the plurality of imaging targets being defined in advance in the guideline; and a first notification unit that performs notification indicating that the imaging target which is not imaged is present in a case where the determination unit determines, for the imaging portion, that the imaging target which is not imaged is present among the plurality of imaging targets which are defined in advance in the guideline.

In the three-dimensional ultrasound imaging support apparatus according to the aspect of the present disclosure, in a case where the determination unit determines, for the imaging portion, that the imaging target which is not imaged is present among the plurality of imaging targets which are defined in advance in the guideline, the first notification unit performs notification indicating the imaging position at which it is possible for the imaging target which is defined in the guideline and is not imaged to be imaged.

In the three-dimensional ultrasound imaging support apparatus according to the aspect of the present disclosure, the first notification unit may perform notification indicating the imaging position and a direction of the ultrasound probe at the imaging position.

In the three-dimensional ultrasound imaging support apparatus according to the aspect of the present disclosure, in a case where an imaging order of the plurality of imaging targets is defined in the guideline for each of the portions and the determination unit determines, by using the plurality of two-dimensional ultrasound images, whether or not all of the plurality of imaging targets which are defined in advance in the guideline are imaged, the determination unit may determine whether or not imaging is performed according to the imaging order which is defined in the guideline each time the two-dimensional ultrasound image is imaged, and the first notification unit may perform notification according to a result of the determination.

The three-dimensional ultrasound imaging support apparatus according to the aspect of the present disclosure may further include a speed detection unit that detects whether or not the ultrasound probe is moving at a predetermined speed based on the imaging position acquired by the imaging position acquisition unit; and a second notification unit that performs notification indicating that the ultrasound probe is not moving at the predetermined speed in a case where the speed detection unit detects that the ultrasound probe is not moving at the predetermined speed.

In the three-dimensional ultrasound imaging support apparatus according to the aspect of the present disclosure, in a case where the imaging portion is estimated by the estimation unit, the speed detection unit may detect whether or not the ultrasound probe is moving at a speed which is predetermined for the estimated imaging portion.

The three-dimensional ultrasound imaging support apparatus according to the aspect of the present disclosure may further include a marker member that is fixed to the ultrasound probe, and an image capturing unit that captures an image of the ultrasound probe and the marker member within the same image capturing range. The imaging position acquisition unit may acquire the imaging position based on a captured image in which the ultrasound probe and the marker member are included and which is acquired by the image capturing unit.

The three-dimensional ultrasound imaging support apparatus according to the aspect of the present disclosure may further include a six-axis sensor that is provided on the ultrasound probe. The imaging position acquisition unit may acquire the imaging position based on output information which is output from the six-axis sensor.

The three-dimensional ultrasound imaging support apparatus according to the aspect of the present disclosure may further include a marker member that is fixed to the ultrasound probe, a six-axis sensor that is provided on the ultrasound probe, and an image capturing unit that captures an image of the ultrasound probe and the marker member within the same image capturing range. The imaging position acquisition unit may acquire the imaging position based on a captured image in which the ultrasound probe and the marker member are included and which is acquired by the image capturing unit and output information which is output from the six-axis sensor.

According to another aspect of the present disclosure, there is provided a three-dimensional ultrasound imaging support method that supports imaging of an ultrasound image by a three-dimensional ultrasound apparatus for generating a three-dimensional ultrasound image, the method including: acquiring a plurality of two-dimensional ultrasound images which are imaged by an ultrasound probe at different positions of a certain portion among a plurality of portions of a subject; acquiring an imaging position of the ultrasound probe for each imaging; generating a three-dimensional ultrasound image based on the plurality of acquired two-dimensional ultrasound images and the acquired imaging position for each imaging; estimating, from the plurality of portions of the subject, an imaging portion corresponding to the two-dimensional ultrasound image and to the three-dimensional ultrasound image, based on at least one of the acquired two-dimensional ultrasound image or the generated three-dimensional ultrasound image; determining, by using a guideline in which a plurality of imaging targets to be imaged are defined in advance for each of the portions of the subject, for the estimated imaging portion, whether or not all of the plurality of imaging targets are imaged in at least one of the plurality of two-dimensional ultrasound images or the three-dimensional ultrasound image, the plurality of imaging targets being defined in advance in the guideline; and performing notification indicating that the imaging target which is not imaged is present in a case where it is determined that, for the imaging portion, the imaging target which is not imaged is present among the plurality of imaging targets which are defined in advance in the guideline.

According to still another aspect of the present disclosure, there is provided a three-dimensional ultrasound imaging support program that supports imaging of an ultrasound image by a three-dimensional ultrasound apparatus for generating a three-dimensional ultrasound image, the program causing a computer to function as: an image acquisition unit that acquires a plurality of two-dimensional ultrasound images which are imaged by an ultrasound probe at different positions of a certain portion among a plurality of portions of a subject; an imaging position acquisition unit that acquires an imaging position of the ultrasound probe for each imaging; a three-dimensional ultrasound image generation unit that generates a three-dimensional ultrasound image based on the plurality of two-dimensional ultrasound images which are acquired by the image acquisition unit and the imaging position for each imaging which is acquired by the imaging position acquisition unit; an estimation unit that estimates, from the plurality of portions of the subject, an imaging portion corresponding to the two-dimensional ultrasound image and to the three-dimensional ultrasound image, based on at least one of the two-dimensional ultrasound image acquired by the image acquisition unit or the three-dimensional ultrasound image generated by the three-dimensional ultrasound image generation unit; a determination unit that determines, by using a guideline in which a plurality of imaging targets to be imaged are defined in advance for each of the portions of the subject, for the imaging portion estimated by the estimation unit, whether or not all of the plurality of imaging targets are imaged in at least one of the plurality of two-dimensional ultrasound images or the three-dimensional ultrasound image, the plurality of imaging targets being defined in advance in the guideline; and a first notification unit that performs notification indicating that the imaging target which is not imaged is present in a case where the determination unit determines, for the imaging portion, that the imaging target which is not imaged is present among the plurality of imaging targets which are defined in advance in the guideline.

According to still another aspect of the present disclosure, there is provided a three-dimensional ultrasound imaging support apparatus including: a memory that stores a command to be executed by a computer; and a processor configured to execute the stored command, in which the processor is configured to execute processing of acquiring a plurality of two-dimensional ultrasound images which are imaged by an ultrasound probe at different positions of a certain portion among a plurality of portions of a subject, acquiring an imaging position of the ultrasound probe for each imaging, generating a three-dimensional ultrasound image based on the plurality of acquired two-dimensional ultrasound images and the acquired imaging position for each imaging, estimating, from the plurality of portions of the subject, an imaging portion corresponding to the two-dimensional ultrasound image and to the three-dimensional ultrasound image, based on at least one of the acquired two-dimensional ultrasound image or the generated three-dimensional ultrasound image, determining, by using a guideline in which a plurality of imaging targets to be imaged are defined in advance for each of the portions of the subject, for the estimated imaging portion, whether or not all of the plurality of imaging targets are imaged in at least one of the plurality of two-dimensional ultrasound images or the three-dimensional ultrasound image, the plurality of imaging targets being defined in advance in the guideline, and performing notification indicating that the imaging target which is not imaged is present in a case where it is determined that, for the imaging portion, the imaging target which is not imaged is present among the plurality of imaging targets which are defined in advance in the guideline.

According to the three-dimensional ultrasound imaging support apparatus, the three-dimensional ultrasound imaging support method, and the three-dimensional ultrasound imaging support program, the user can easily confirm whether or not all of the imaging targets conforming to the guideline are imaged.

DESCRIPTION OF THE PREFERRED EMBODIMENTS

Figure 1:
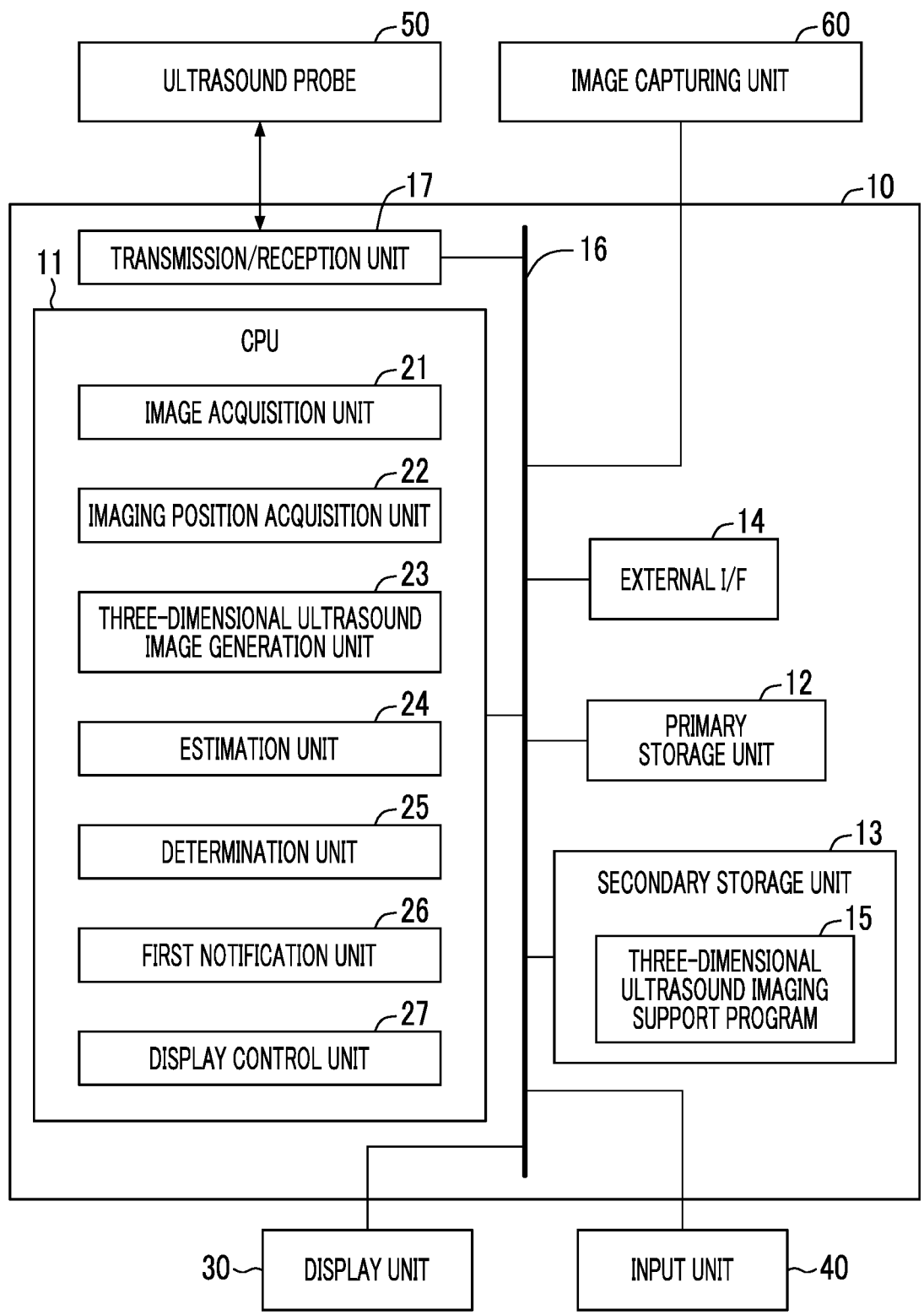
FIG. 1 is a schematic block diagram illustrating a configuration of a diagnosis support system including a three-dimensional ultrasound imaging support apparatus according to a first embodiment of the present disclosure.

Hereinafter, embodiments of the present disclosure will be described with reference to the drawings. FIG. 1 is a schematic block diagram illustrating a configuration of a diagnosis support system to which a three-dimensional ultrasound imaging support apparatus according to an embodiment of the present disclosure is applied. As illustrated in FIG. 1, a diagnosis support system 1 includes a three-dimensional ultrasound imaging support apparatus 10 according to the present embodiment, an ultrasound probe 50 configured to be connected to the three-dimensional ultrasound imaging support apparatus 10, an image capturing unit 60, a display unit 30, and an input unit 40.

The three-dimensional ultrasound imaging support apparatus 10 is configured with a computer including a central processing unit (CPU) 11, a primary storage unit 12, a secondary storage unit 13, an external interface (I/F) 14, and the like. The CPU 11 controls the entire three-dimensional ultrasound imaging support apparatus 10. The primary storage unit 12 is a volatile memory used as a work area or the like in execution of various programs. As an example of the primary storage unit 12, a random-access memory (RAM) may be used. The secondary storage unit 13 is a non-volatile memory that stores various programs and various parameters in advance, and a three-dimensional ultrasound imaging support program 15 according to an embodiment of the present disclosure is installed in the secondary storage unit 13.

The three-dimensional ultrasound imaging support program 15 is distributed by being recorded on a recording medium such as a digital versatile disc (DVD) or a compact disc read only memory (CD-ROM), and is installed in a computer from the recording medium. Alternatively, the three-dimensional ultrasound imaging support program 15 may be stored in a storage device of a server computer connected to a network or a network storage in a state where access from the outside is allowed, or may be downloaded and installed in a computer according to a request from the outside.

The three-dimensional ultrasound imaging support program 15 is executed by the CPU 11, and thus the CPU 11 functions as an image acquisition unit 21, an imaging position acquisition unit 22, a three-dimensional ultrasound image generation unit 23, an estimation unit 24, a determination unit 25, a first notification unit 26, and a display control unit 27. Examples of the secondary storage unit 13 include an electrically erasable programmable read-only memory (EEPROM), a flash memory, and the like.

The external I/F 14 controls transmission and reception of various information between the three-dimensional ultrasound imaging support apparatus 10 and an external apparatus (not illustrated). The CPU 11, the primary storage unit 12, the secondary storage unit 13, and the external I/F 14 are connected to a bus line 16 which is a common route through which each circuit exchanges data.

The display unit 30 and the input unit 40 are also connected to the bus line 16. The display unit 30 is configured with, for example, a liquid crystal display or the like. As will be described later, the display unit 30 displays a two-dimensional ultrasound image acquired by the image acquisition unit 21 and a three-dimensional ultrasound image generated by the three-dimensional ultrasound image generation unit 23. Further, the display unit 30 displays a captured image acquired by the image capturing unit 60 to be described. The display unit 30 may be configured with a touch panel such that the display unit 30 also serves as the input unit 40. The input unit 40 includes a mouse and a keyboard, and receives various setting input by a user. Further, a transmission/reception unit 17 and the image capturing unit 60 such as camera are also connected to the bus line 16. The transmission/reception unit 17 controls transmission and reception of various information to and from the ultrasound probe 50 to be described.

Figure 2:
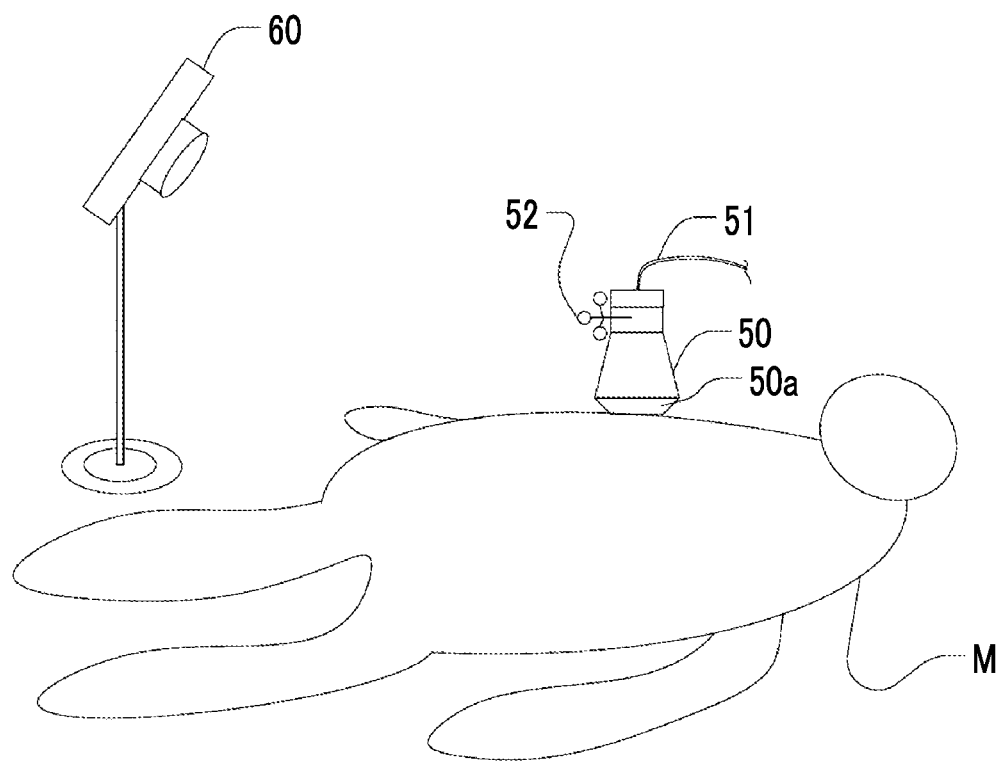
FIG. 2 is a conceptual diagram of the diagnosis support system according to an embodiment of the present disclosure.

The ultrasound probe 50 is configured to be connected to the three-dimensional ultrasound imaging support apparatus 10. As the ultrasound probe 50, for example, a probe for sector scanning, a probe for linear scanning, a probe for convex scanning, and the like may be used. FIG. 2 is a conceptual diagram of the diagnosis support system according to the embodiment of the present disclosure. As illustrated in FIG. 2, the ultrasound probe 50 includes a transducer array 50a which is provided at a distal end and in which a plurality of ultrasound transducers (not illustrated) are arranged in a one-dimensional direction. In the embodiment, an example in which the transducer array 50a includes a plurality of ultrasound transducers one-dimensionally arranged is described. On the other hand, the present disclosure is not limited thereto. In the transducer array 50a, a plurality of ultrasound transducers may be two-dimensionally arranged.

In a state where the transducer array 50a is brought into contact with a body surface of a subject M as a living body, the ultrasound probe 50 emits (transmits) an ultrasound wave to a portion of the subject M to be measured, and detects (receives) the reflected ultrasound wave which is reflected and returned by the subject M. The ultrasound probe 50 converts an electric signal with a pulse wave or a continuous wave that is output from the transmission/reception unit 17 into an ultrasound wave, and emits the converted ultrasound wave. Further, the ultrasound probe 50 converts the reflected ultrasound wave that is received into an electric signal, and transmits the converted electric signal to the transmission/reception unit 17.

The transmission/reception unit 17 transmits, to the ultrasound probe 50, an electric signal with a pulse wave or a continuous wave that is for driving the plurality of ultrasound transducers included in the ultrasound probe 50. Further, the transmission/reception unit 17 receives a plurality of electric signals generated by the plurality of ultrasound transducers that receive the reflected ultrasound wave. The transmission/reception unit 17 generates a reception signal by performing amplification and analog/digital (A/D) conversion on the received electric signal. The reception signal is, for example, a signal including a plurality of signals that are arranged in an arrangement direction of the ultrasound transducers and in a direction which is a transmission direction of the ultrasound wave and which is perpendicular to the arrangement direction of the ultrasound transducers (hereinafter, referred to as a depth direction). Each signal of the plurality of signals is a digital signal which represents, as a digital value, an amplitude of the reflected ultrasound wave. The transmission processing and the reception processing are repeatedly and continuously performed, and thus a plurality of pieces of frame data including a plurality of reception signals are generated.

In the present disclosure, the frame data refers to group data of the reception signals required to configure one tomographic image, a signal which is processed to configure tomographic image data based on the group data, or one piece of tomographic image data or a tomographic image which is configured based on the group data. In the present embodiment, the frame data refers to one piece of tomographic image data. The configured tomographic image data is stored in the primary storage unit 12.

Figure 3:
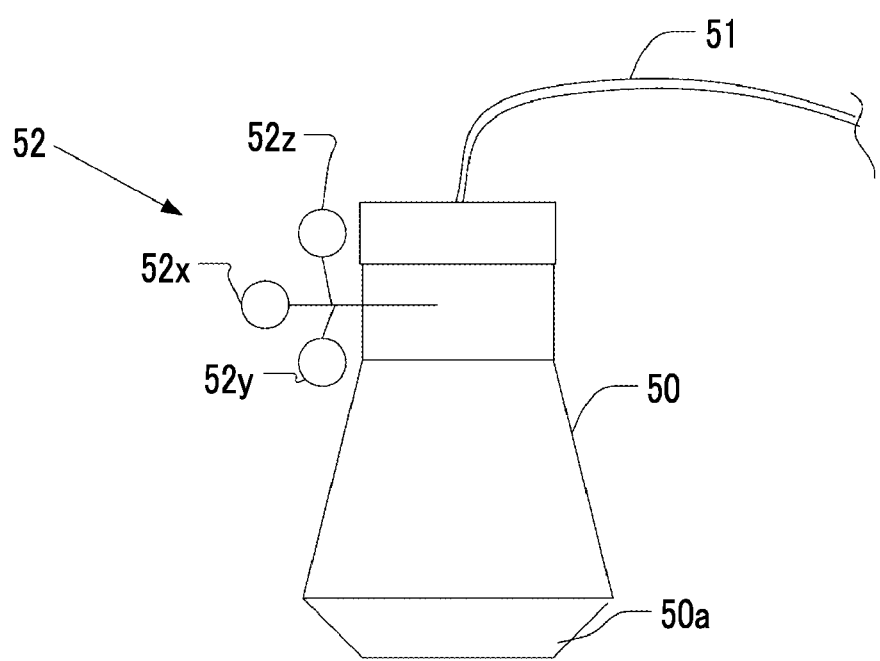
FIG. 3 is a diagram for explaining an ultrasound probe to which a marker member is fixed.

Further, in the present embodiment, a marker member is fixed to the ultrasound probe 50. FIG. 3 is a diagram for explaining the ultrasound probe 50 to which a marker member is fixed according to an embodiment of the present disclosure. In FIG. 3, a portion at which the marker member is fixed to the ultrasound probe 50 is illustrated in a simple manner, unlike an actual shape.

As illustrated in FIG. 3, the ultrasound probe 50 includes a cable 51 for connection with the transmission/reception unit 17. Further, a marker member 52 is fixed to an outer circumferential surface of the ultrasound probe 50. The marker member 52 includes three spherical markers, that is, a marker 52x, a marker 52y, and a marker 52z, and three axes of an x-axis, a y-axis, and a z-axis of which axial directions are orthogonal to each other. The three markers of the marker 52x, the marker 52y, and the marker 52z are respectively provided at one ends of the three axes of the x-axis, the y-axis, and the z-axis, with a marker center 52a as a center of the markers. The other ends of the three axes of the x-axis, the y-axis, and the z-axis are provided on a column provided on the ultrasound probe 50. Further, the three markers of the marker 52x, the marker 52y, and the marker 52z are colored, for example, in different colors, and can be identified by the colors.

In the present embodiment, a configuration in which the marker member 52 includes the three markers of the marker 52x, the marker 52y, and the marker 52z is described. On the other hand, the technique of the present disclosure is not limited thereto, and markers other than the three markers may be used. For example, four or five markers may be used. Further, the shape of the marker is not limited to a spherical shape, and may be, for example, a rectangular parallelepiped shape or a conical shape, and may be appropriately changed.

Figure 4:
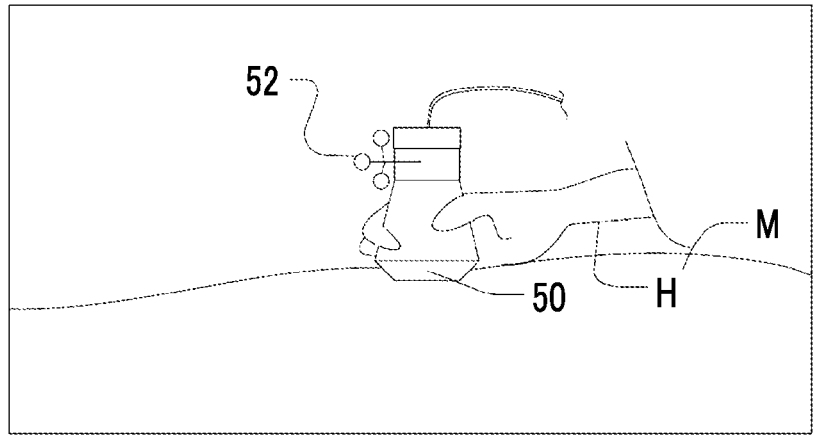
FIG. 4 is a diagram illustrating an example of an image acquired by an image capturing unit.

The image capturing unit 60 illustrated in FIG. 2 is provided at a position at which the ultrasound probe 50 and the marker member 52 can be captured together within the same image capturing range. FIG. 4 is a diagram illustrating an example of an image acquired by the image capturing unit 60. As illustrated in FIG. 4, in an image D acquired by the image capturing unit 60, the ultrasound probe 50 that is held by a hand H of the user and that is brought into contact with a body surface of the subject M and the marker member 52 that is fixed to the ultrasound probe 50 appear.

Figure 5:
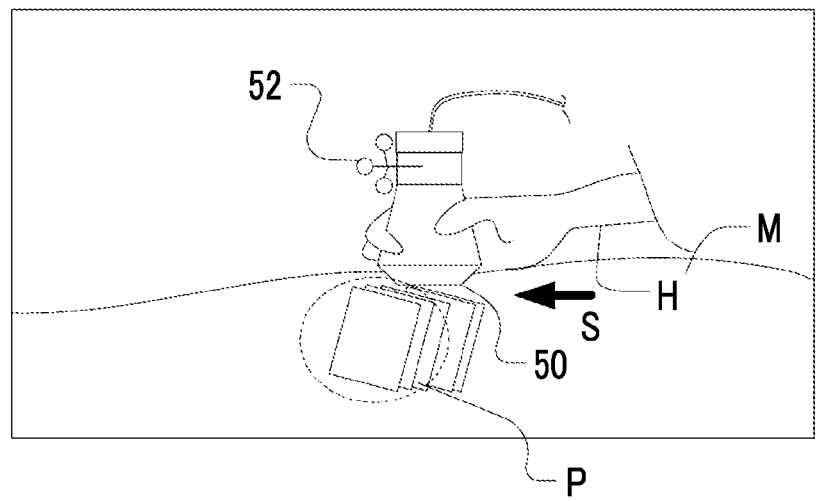
FIG. 5 is a diagram for explaining an imaging operation by the ultrasound probe.

FIG. 5 is a diagram for explaining an imaging operation by the ultrasound probe 50. As illustrated in FIG. 5, in a state where the ultrasound probe 50 is brought into contact with the body surface of the subject M by the user, imaging is performed at different positions by moving the ultrasound probe 50 in a direction indicated by, for example, an arrow S. A plurality of two-dimensional ultrasound images P are acquired at a plurality of different imaging positions at which imaging is performed. The imaging position is a position of the ultrasound probe 50 on the body surface for each imaging. The two-dimensional ultrasound image P is a tomographic image having a cross section extending in a depth direction from each imaging position to the inside of the subject.

Returning to FIG. 2, the image acquisition unit 21 acquires the two-dimensional ultrasound images P which are imaged by the ultrasound probe 50 at each imaging position. The two-dimensional ultrasound image P is a tomographic image having a cross section extending in a depth direction from each imaging position to the inside of the subject. The ultrasound probe 50 outputs, to the primary storage unit 12, the plurality of two-dimensional ultrasound images P (tomographic images) which are imaged. The image acquisition unit 21 acquires the two-dimensional ultrasound images P (tomographic images) from the primary storage unit 12.

The imaging position acquisition unit 22 acquires an imaging position of the ultrasound probe 50. Specifically, at each of different imaging positions, the image capturing unit 60 captures the ultrasound probe 50 and the marker member 52. A captured image which is obtained by capturing the ultrasound probe 50 and the marker member 52 is output to the primary storage unit 12. The imaging position acquisition unit 22 reads the captured image from the primary storage unit 12. The imaging position acquisition unit 22 derives information including the imaging position and the direction of the ultrasound probe 50, from a position of a marker center 52*a*, and positions, sizes, and inclinations of the markers 52*x*, 52*y*, and 52*z* in the captured image, by performing image analysis on the captured image which is read. The imaging position acquisition unit 22 identifies each marker of the markers 52*x*, 52*y*, and 52*z* by color. The imaging position acquisition unit 22 acquires information including the imaging position and the direction via derivation processing.

Figure 6:
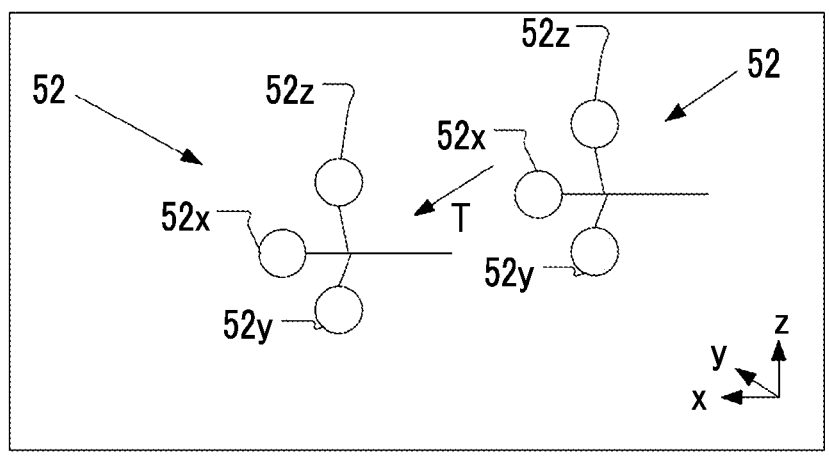
FIG. 6 is a diagram for explaining movement of the marker member 52 in a captured image.

FIG. 6 is a diagram for explaining movement of the marker member 52 in the captured image. In a case where the ultrasound probe 50 acquires the two-dimensional ultrasound images P at an imaging position T1 and an imaging position T2, for example, as illustrated in FIG. 6, the marker member 52 moves in a direction of an arrow T in the captured image. In this case, a position of the ultrasound probe 50 in an x direction is derived from an amount of movement of the marker center 52*a* in the x direction. In addition, a position of the ultrasound probe 50 in a y direction is derived from an amount of change in the sizes of the markers 52*x*, 52*y*, and 52*z*. Further, an amount of rotation of the marker member 52 is detected from a movement trajectory of the marker center 52*a* of the markers 52*x*, 52*y*, and 52*z*. The direction of the ultrasound probe 50 is derived based on an amount of rotation. The derived information including the imaging position and the direction of the ultrasound probe 50 is stored in the primary storage unit 12 by being associated with the two-dimensional ultrasound image P which is acquired at the imaging position. As a method of acquiring information including the imaging position and the direction of the ultrasound probe 50 using the marker member 52, a known technique may be used.

The three-dimensional ultrasound image generation unit 23 generates a three-dimensional ultrasound image V for a space determined by an angle range or a stroke of mechanical scanning of the transducer array 50*a* and an electronic scanning range of the transducer array 50*a*, by using the two-dimensional ultrasound image P acquired by the image acquisition unit 21 and the information that is stored in the primary storage unit 12 by being associated with the two-dimensional ultrasound image P and that includes the imaging position and the direction of the ultrasound probe 50. As a method of generating the three-dimensional ultrasound image V, a known technique may be used. Here, the information including the imaging position and the direction of the ultrasound probe 50 may be collectively referred to as position information of the ultrasound probe 50.

The estimation unit 24 estimates, from a plurality of portions of the subject, an imaging portion corresponding to the two-dimensional ultrasound image P and to the three-dimensional ultrasound image V, based on at least one of the two-dimensional ultrasound image P acquired by the image acquisition unit 21 or the three-dimensional ultrasound image V generated by the three-dimensional ultrasound image generation unit 23.

In a method of estimating an imaging portion, a plurality of collation patterns are prepared in advance by being associated with, for example, a plurality of prestored imaging portions such as a blood vessel (a carotid artery, a jugular vein, or the like), a heart, a liver, a kidney, a gallbladder, a pancreas, a stomach, a lung, a bladder, a thyroid, and a breast, that is, imaging portions which are generally examined. In this case, a method of recognizing an imaging portion by collating the acquired two-dimensional ultrasound image P or the generated three-dimensional ultrasound image V with the plurality of collation patterns (for example, a technique described in WO2017/158998A) may be used. Further, a method of estimating an imaging portion by using a learning model, which is trained so as to receive a two-dimensional ultrasound image P and a three-dimensional ultrasound image V and to output an imaging portion corresponding to the two-dimensional ultrasound image P and to the three-dimensional ultrasound image V, may be used.

By using a guideline in which a plurality of imaging targets to be imaged are defined in advance for each portion of a subject, the determination unit 25 determines, for the imaging portion estimated by the estimation unit 24, whether or not all of a plurality of imaging targets are imaged in at least one of the plurality of two-dimensional ultrasound images P or the three-dimensional ultrasound image V, the plurality of imaging targets being defined in advance in the guideline.

In the guideline, for example, in a case where an imaging portion is a carotid artery, it is defined that a tomographic image is observed in two directions of a minor-axis cross section direction of a blood vessel and a major-axis cross section direction of a blood vessel, and it is defined that observation regions include a common carotid artery, a carotid sinus, an internal carotid artery, and a vertebral artery as regions which can be observed on both right and left sides. Further, it is also defined that observation regions include an external carotid artery, a subclavian artery, a brachiocephalic artery, a superficial temporal artery, and a branch artery of the arteries, as necessary. As described above, in the guideline, a plurality of imaging targets to be imaged, such as a common carotid artery and a carotid sinus in the observation region, are defined for each portion of the subject such as a carotid artery. In the present embodiment, based on the guideline, a list for the plurality of imaging targets to be imaged is created in advance for each imaging portion. The list is stored in the primary storage unit 12.

Further, in the present embodiment, the determination unit 25 classifies structures included in the two-dimensional ultrasound image P and the three-dimensional ultrasound image V. For example, in a case where the imaging portion is a carotid artery, the structures include a common carotid artery, a carotid sinus, an internal carotid artery, and a vertebral artery. As a method of classifying the structures, for example, as in a method described in JP2018-139693A, classification means for classifying an imaging portion into a plurality of classes by using a neural network which is trained using training data for a two-dimensional ultrasound image P may be used. The determination unit 25 recognizes the imaging targets included in the two-dimensional ultrasound image P by classifying the structures.

Further, as the training data, training data including pairs of two-dimensional ultrasound images and direction information indicating an imaging direction of each image of the two-dimensional ultrasound images may be used, the two-dimensional ultrasound images being imaged in two directions of a minor-axis cross section direction of a blood vessel and a major-axis cross section direction of a blood vessel. By learning the training data by using the classification means of the determination unit 25, it is possible to classify the imaging directions of the two-dimensional ultrasound images P.

The determination unit 25 determines whether or not the plurality of imaging targets included in the two-dimensional ultrasound images P conform to the guideline. Specifically, the determination unit 25 collates the plurality of imaging targets included in the plurality of two-dimensional ultrasound images P acquired by the image acquisition unit 21 and the plurality of imaging targets to be imaged which are defined in the list. The determination unit 25 determines, based on a collation result, for the imaging portion estimated by the estimation unit 24, whether or not all of the plurality of imaging targets which are defined in advance in the guideline are imaged. Further, in the present embodiment, the determination unit 25 performs the determination at a stage at which all of the plurality of two-dimensional ultrasound images P for one imaging portion are imaged.

In a case where the determination unit 25 determines, for the imaging portion, that the imaging target which is not imaged is present among the plurality of imaging targets which are defined in advance in the guideline, the first notification unit 26 performs notification indicating that the imaging target which is not imaged is present. The notification by the first notification unit 26 may be performed by, for example, sounding an alarm via a sound output unit (not illustrated), or the display unit 30 may display "There is an imaging target which is not imaged". Thereby, the user can easily confirm whether or not all of the imaging targets conforming to the guideline are imaged.

In addition to the presence or absence of the imaging target, the first notification unit 26 may perform notification indicating an imaging position at which the imaging target which is defined in the guideline and is not imaged can be imaged. For example, it is assumed that the plurality of imaging targets defined in the guideline include a first imaging target, a second imaging target, and a third imaging target, and that the first imaging target, the second imaging target, and the third imaging target are arranged in this order. Further, it is assumed that the determination unit 25 determines that the second imaging target is not imaged. In this case, two two-dimensional ultrasound images including the first imaging target and the third imaging target are associated with each imaging position, that is, coordinate position information of the marker member 52. Thus, the determination unit 25 can estimate which imaging target can be imaged in a case where the marker member 52 is located at a position. In the example, the determination unit 25 estimates an imaging position at which the second imaging target can be imaged.

The first notification unit 26 causes the display unit 30 to display, as an imaging position at which the second imaging target can be imaged and which is estimated by the determination unit 25, the position of the marker member 52. Further, the first notification unit 26 can perform notification indicating the imaging position and the direction of the ultrasound probe 50 at the imaging position. For example, it is assumed that the guideline defines that a first imaging target, a second imaging target, and a third imaging target which are imaged in two directions are required. In a case where the determination unit 25 determines that the second imaging target in the first direction is not imaged, the first notification unit 26 performs notification indicating the direction of the ultrasound probe 50, the direction being a direction in which the second imaging target from the first direction can be imaged.

Figure 7:
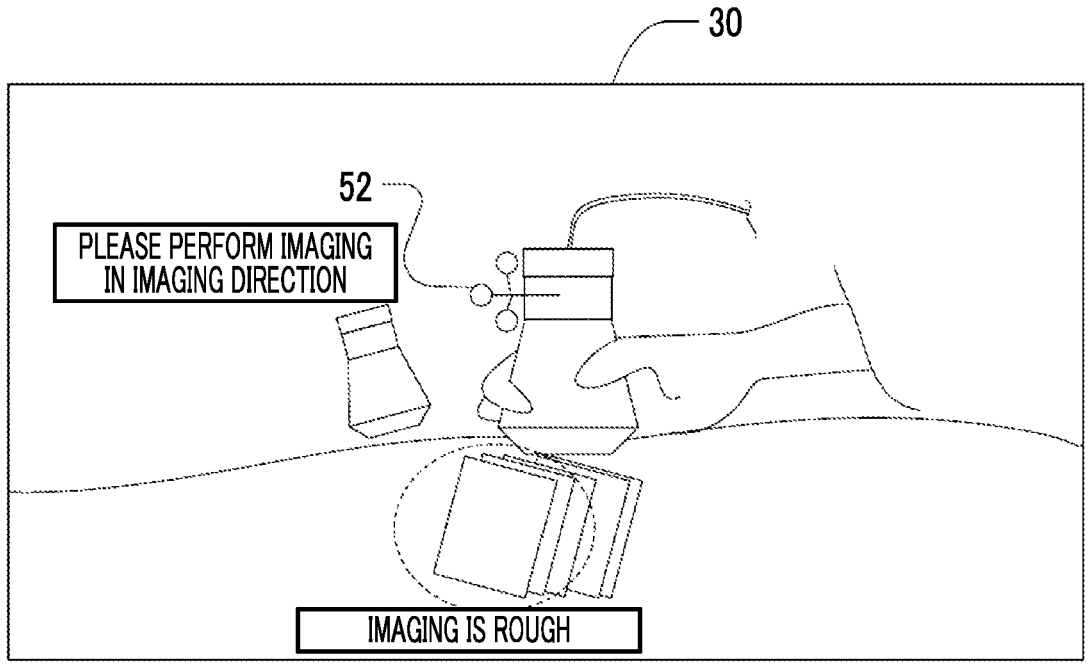
FIG. 7 is a diagram illustrating an example of notification by a first notification unit.
Figure 8:
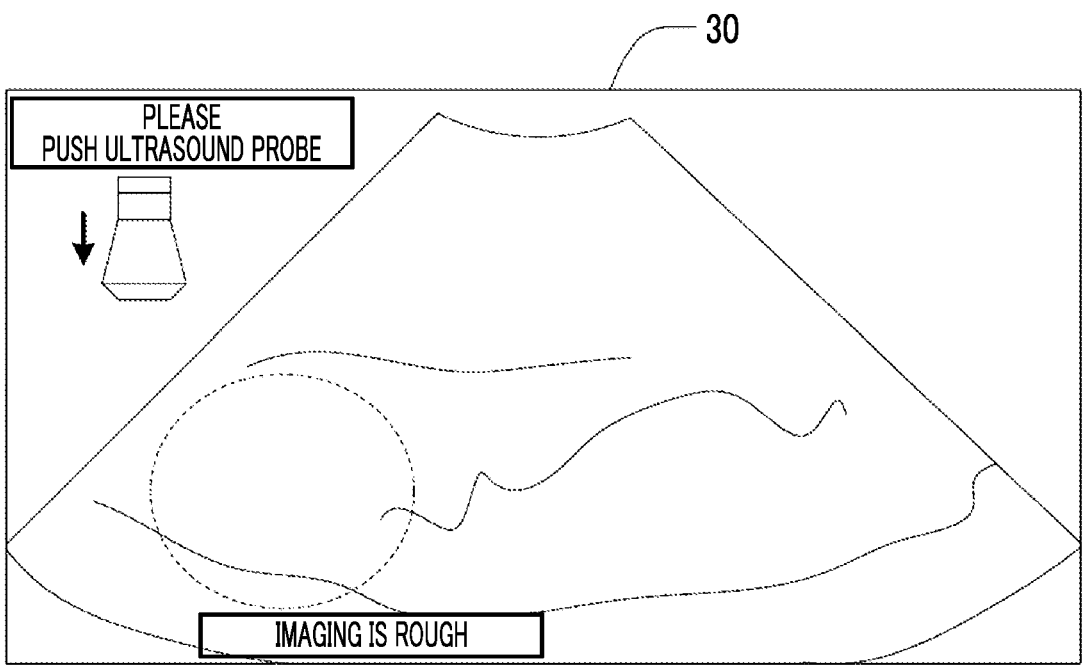
FIG. 8 is a diagram illustrating another example of notification by the first notification unit.

FIG. 7 and FIG. 8 are diagrams illustrating an example of notification by the first notification unit 26. In FIG. 7, an image captured in real time by the image capturing unit 60 is displayed on the display unit 30. As illustrated in FIG. 7, the first notification unit 26 causes the display unit 30 to display, as a mark such as a dotted circle, an imaging position at which an imaging target which is defined in the guideline and is not imaged can be imaged, and to display a message indicating "imaging is rough". Further, the direction in which the imaging target can be imaged is displayed by using a simple image schematically illustrating the ultrasound probe 50. The simple image illustrates a posture of the ultrasound probe 50 that corresponds to the direction in which the imaging target can be imaged. Thereby, the user can confirm the imaging position at which the imaging target to be imaged can be imaged and the direction in which the imaging target to be imaged can be imaged. Therefore, the user can easily move the ultrasound probe 50 to a target position.

In FIG. 8, a two-dimensional ultrasound image imaged in real time by the ultrasound probe 50 is displayed on the display unit 30. As illustrated in FIG. 8, in a case where an imaging target is defined in the guideline and the image is rough, the first notification unit 26 causes the display unit 30 to display a dotted circle, and to display a message indicating "imaging is rough". Generally, it is considered that a rough image is obtained in a case where the ultrasound probe 50 is insufficiently pushed in a depth direction. For this reason, an arrow indicating a direction in which the ultrasound probe 50 is moved in the depth direction and a simple image of the ultrasound probe 50 are displayed. Thereby, the user can visually recognize the direction in which the ultrasound probe 50 is to be moved. Therefore, the user can easily move the ultrasound probe 50 to a target position.

Returning to FIG. 2, the display control unit 27 causes the display unit 30 to display at least one of the two-dimensional ultrasound image P which is imaged by the ultrasound probe 50 or the three-dimensional ultrasound image V. Further, the display control unit 27 causes the display unit 30 to display the image captured by the image capturing unit 60. The display control unit 27 may cause one display unit 30 to display at least one of the two-dimensional ultrasound image P which is imaged by the ultrasound probe 50 or the three-dimensional ultrasound image V, and the image captured by the image capturing unit 60. In a case where there are two display units 30, each display unit may display the ultrasound images.

Figure 9:
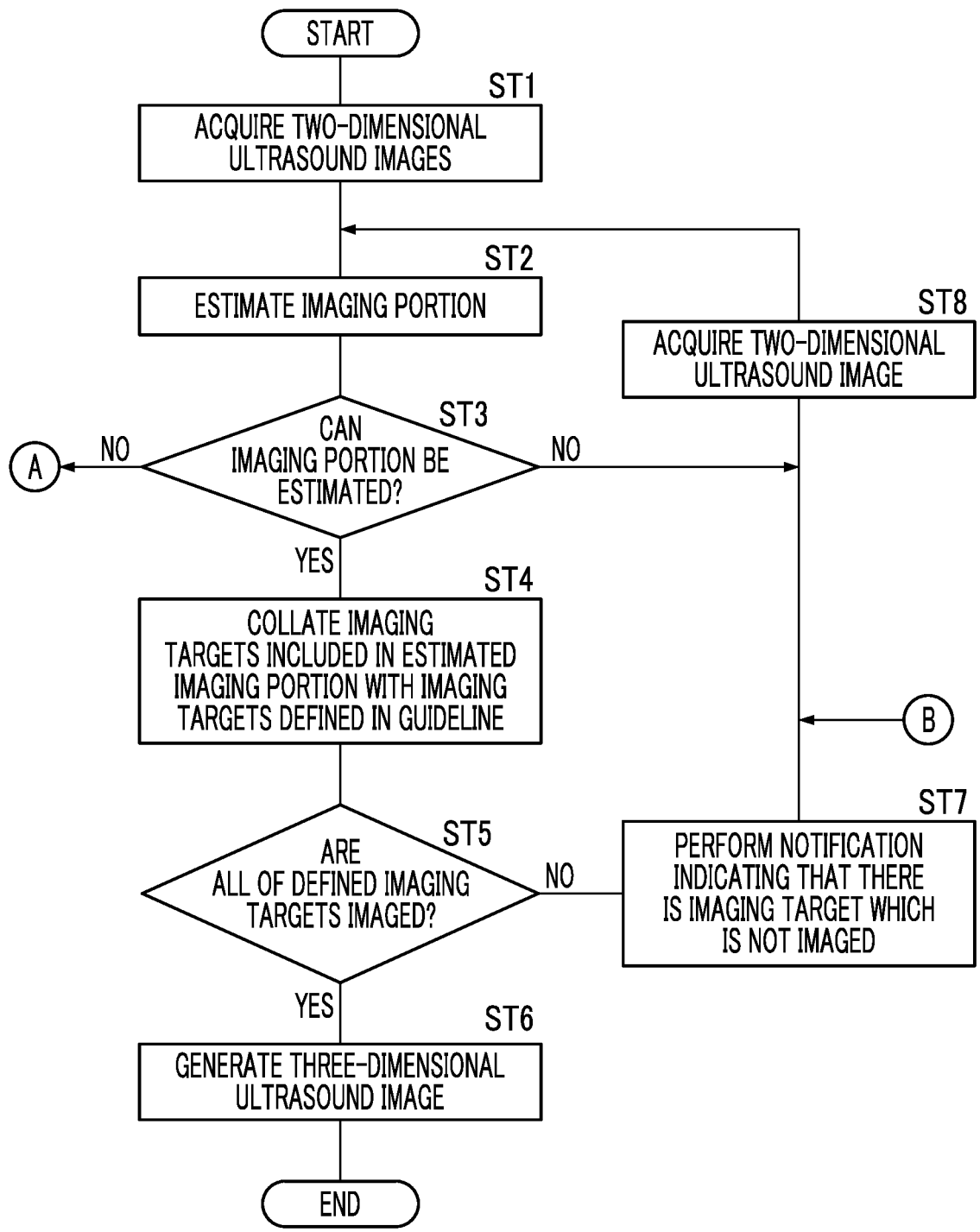
FIG. 9 is a flowchart illustrating processing performed in the first embodiment of the present disclosure.

Next, processing performed in the present embodiment will be described. FIG. 9 is a flowchart illustrating processing performed in the first embodiment of the present disclosure.

In a case where the user operates the ultrasound probe 50 in a state where the ultrasound probe 50 is brought into contact with the body surface of the subject M, the image acquisition unit 21 acquires two-dimensional ultrasound images P obtained by imaging (step ST1). At this time, the imaging position acquisition unit 22 acquires an imaging position of the ultrasound probe 50.

Next, an imaging portion is estimated in the acquired two-dimensional ultrasound image P (step ST2). In a case where the imaging portion cannot be estimated (NO in step ST3), the image acquisition unit 21 acquires a two-dimensional ultrasound image P which is imaged by operating the ultrasound probe 50 at a different position (step ST8). Then, the CPU 11 transitions to processing of step ST2, and performs subsequent processing. Further, the CPU 11 performs processing A in parallel. The processing A will be described later.

Next, in a case where the imaging portion can be estimated (YES in step ST3), the determination unit 25 collates imaging targets included in the estimated imaging portion of the two-dimensional ultrasound image P with imaging targets which are defined in the guideline (step ST4). In a case where all of the defined imaging targets are imaged (YES in step ST5), the three-dimensional ultrasound image generation unit 23 generates a three-dimensional ultrasound image V based on the two-dimensional ultrasound image P acquired by the image acquisition unit 21 and an imaging position of the ultrasound probe 50 while the two-dimensional ultrasound image P is imaged (step ST6). Then, the processing is completed.

On the other hand, in a case where not all of the defined imaging targets are imaged (NO in step ST5), that is, in a case where the imaging target which is not imaged is present, the first notification unit 26 performs notification indicating that the imaging target which is not imaged is present (step ST7).

Next, the image acquisition unit 21 acquires the two-dimensional ultrasound image P which is imaged by operating the ultrasound probe 50 (step ST8). Then, the CPU 11 transitions to processing of step ST2, and performs subsequent processing. In the imaging, as described above, the first notification unit 26 performs notification indicating an imaging position at which the imaging target which is not imaged can be imaged.

Figure 10:
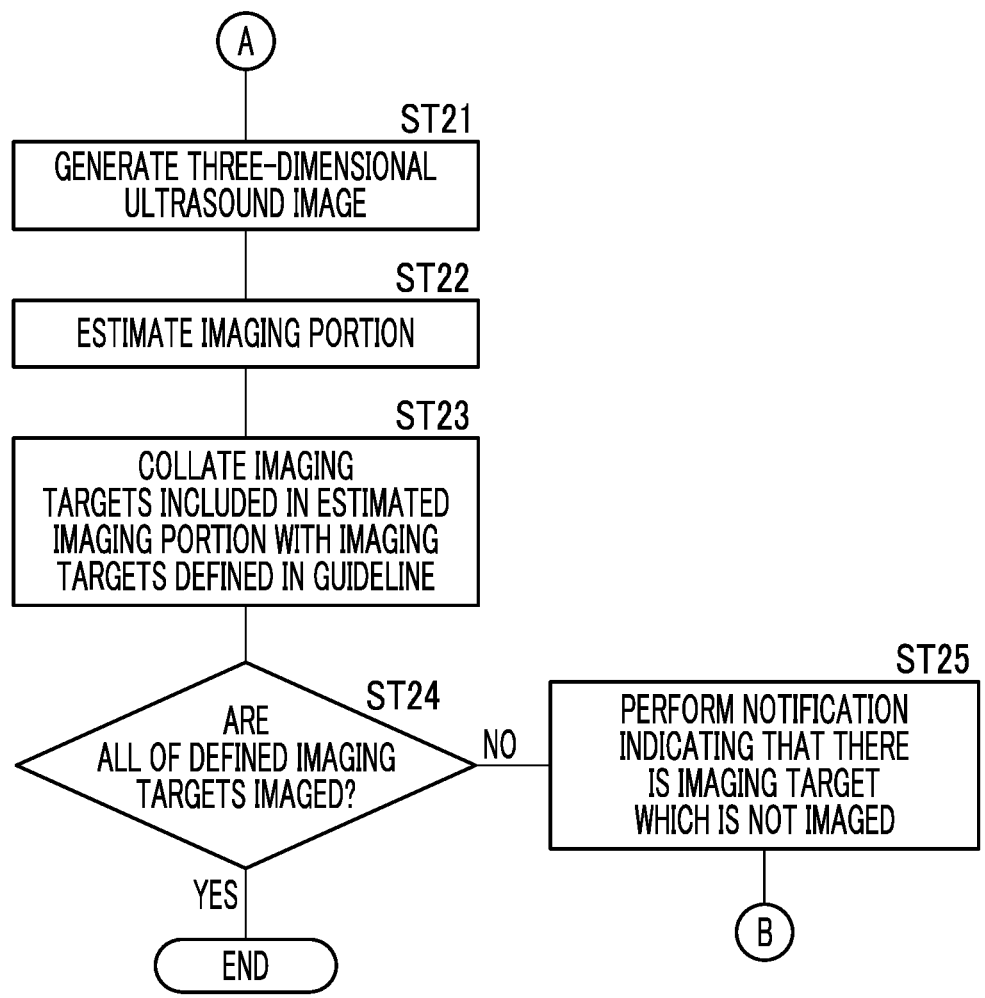
FIG. 10 is a flowchart illustrating processing A performed in the first embodiment of the present disclosure.

Next, in step ST3, in a case where the imaging portion cannot be estimated (NO in step ST3), processing A is performed. FIG. 10 is a flowchart illustrating processing A performed in the first embodiment of the present disclosure.

As illustrated in FIG. 10, the three-dimensional ultrasound image generation unit 23 generates a three-dimensional ultrasound image V based on the two-dimensional ultrasound image P acquired by the image acquisition unit 21 and an imaging position of the ultrasound probe 50 while the two-dimensional ultrasound image P is imaged (step ST21). Then, an imaging portion is estimated in the acquired three-dimensional ultrasound image V (step ST22).

Next, the determination unit 25 collates imaging targets included in the imaging portion estimated in the three-dimensional ultrasound image V with imaging targets which are defined in the guideline (step ST23). In a case where all of the defined imaging targets are imaged (YES in step ST24), the processing is ended. On the other hand, in a case where all of the defined imaging targets are not imaged (NO in step ST24), that is, in a case where the imaging target which is not imaged is present, the first notification unit 26 performs notification indicating that the imaging target which is not imaged is present (step ST25). Then, the CPU 11 transitions to processing of step ST8 of FIG. 9, and performs the subsequent processing.

In general, it is known that an imaging portion can be specified in the three-dimensional ultrasound image V even in a case where an imaging portion cannot be estimated in the two-dimensional ultrasound image P. For this reason, in a case where an imaging portion cannot be estimated in the two-dimensional ultrasound image P, by specifying an imaging portion in the three-dimensional ultrasound image V, the determination unit 25 can collate imaging targets included in the specified imaging portion with the imaging targets based on the guideline for each imaging portion. Thereby, the determination unit 25 can determine, for the imaging portion, whether or not all of the plurality of imaging targets which are defined in advance in the guideline are imaged.

In the first embodiment, in a case where the imaging portion cannot be estimated in the two-dimensional ultrasound image P, the processing A illustrated in FIG. 10 is performed. On the other hand, the technique of the present disclosure is not limited thereto. Even in a case where the imaging portion can be estimated in the two-dimensional ultrasound image P, the processing A illustrated in FIG. 10 may be performed. By estimating the imaging portion in both of the two-dimensional ultrasound image P and the three-dimensional ultrasound image V, the imaging portion can be estimated with higher accuracy.

Figure 11:
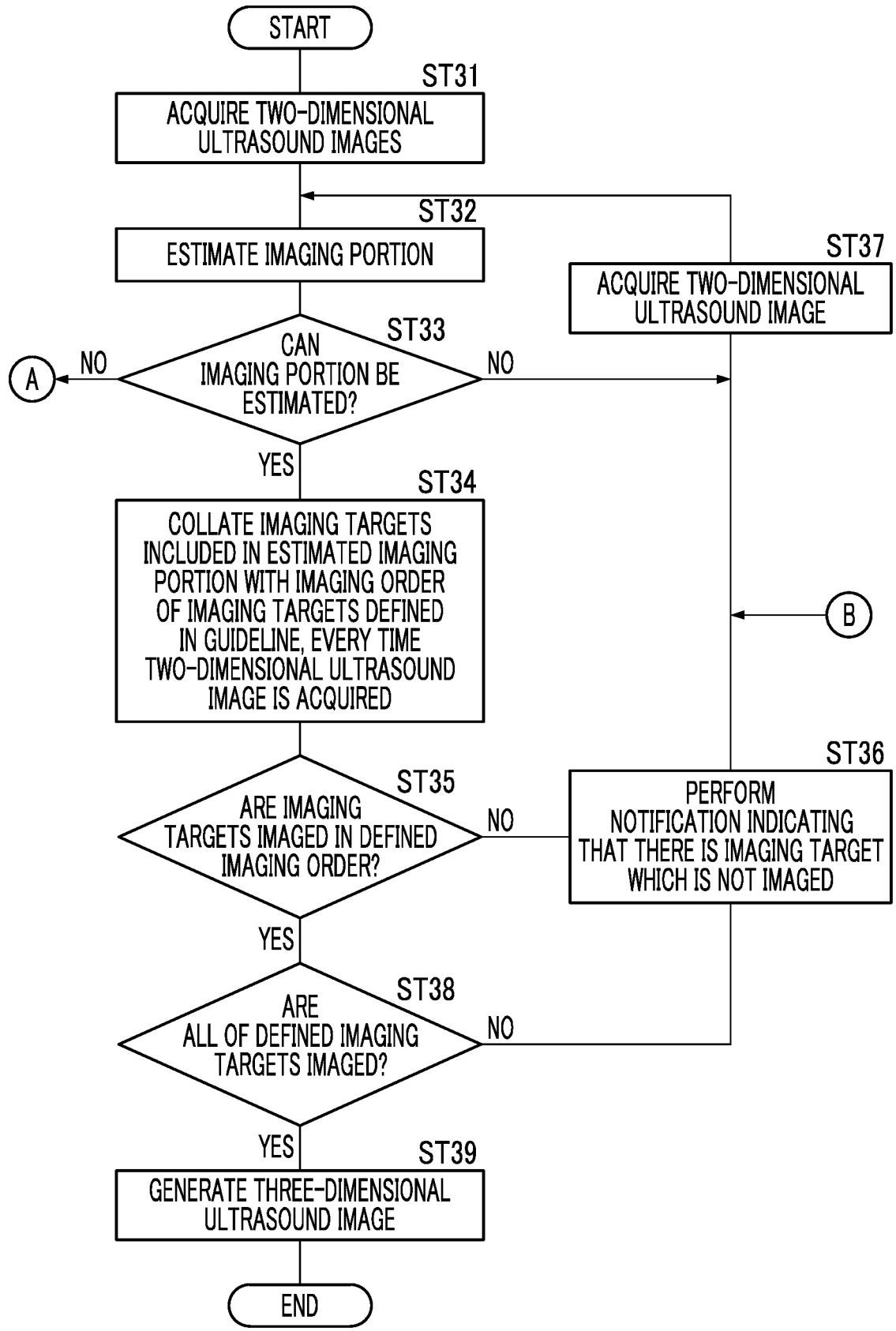
FIG. 11 is a flowchart illustrating processing performed in a second embodiment of the present disclosure.

Next, the three-dimensional ultrasound imaging support apparatus according to a second embodiment will be described. The three-dimensional ultrasound imaging support apparatus according to the second embodiment creates a list in which a plurality of imaging targets to be imaged in advance are listed in an imaging order, for each imaging portion, based on the guideline. The list is stored in the primary storage unit 12. The three-dimensional ultrasound imaging support apparatus according to the second embodiment may have the same configuration as the three-dimensional ultrasound imaging support apparatus 10 according to the first embodiment illustrated in FIG. 1. For this reason, a description of the configuration will be omitted, and only processing performed in the three-dimensional ultrasound imaging support apparatus according to the second embodiment will be described. FIG. 11 is a flowchart illustrating processing performed in the second embodiment of the present disclosure. Since processing of step ST31 to step ST33 in FIG. 11 is the same as the processing of step ST1 to step ST3 in FIG. 9, a description thereof will be omitted.

As illustrated in FIG. 11, in step ST33, in a case where an imaging portion can be estimated (YES in step ST33), every time the image acquisition unit 21 acquires the two-dimensional ultrasound image P, the determination unit 25 collates imaging targets included in the estimated imaging portion of the acquired two-dimensional ultrasound image P with the imaging order of the imaging targets which are defined in the guideline (step ST34).

In a case where the imaging targets included in the estimated imaging portion are not imaged in the defined imaging order (NO in step ST35), that is, in a case where the imaging target which is not imaged is present, the first notification unit 26 performs notification indicating that the imaging target which is not imaged is present (step ST36).

Next, the image acquisition unit 21 acquires the two-dimensional ultrasound image P which is imaged by operating the ultrasound probe 50 (step ST37). Then, the CPU 11 transitions to processing of step ST32, and performs subsequent processing. In the imaging, as described above, the first notification unit 26 performs notification indicating an imaging position at which the imaging target which is not imaged can be imaged.

On the other hand, in a case where the imaging targets included in the estimated imaging portion are imaged in the defined imaging order (YES in step ST35), the determination unit 25 determines whether or not all of the defined imaging targets are imaged (step ST38). In a case where all of the defined imaging targets are imaged (YES in step ST38), the three-dimensional ultrasound image generation unit 23 generates a three-dimensional ultrasound image V based on the two-dimensional ultrasound image P acquired by the image acquisition unit 21 and an imaging position of the ultrasound probe 50 while the two-dimensional ultrasound image P is imaged (step ST39). Then, the processing is completed.

On the other hand, in a case where all of the defined imaging targets are not imaged (NO in step ST38), that is, in a case where the imaging target which is not imaged is present, the first notification unit 26 performs notification indicating that the imaging target which is not imaged is present (step ST36). Then, subsequent processing is performed.

In the second embodiment, each time a two-dimensional ultrasound image P is acquired, it is determined whether or not imaging is performed according to the imaging order which is defined in the guideline, and in a case where imaging is not performed according to the imaging order, notification indicating that imaging is not performed according to the imaging order is performed. Therefore, the user can recognize that an imaging position for imaging, in other words, an imaging target, exists between the current imaging position and the previous imaging position. Thus, when the user recognizes that an imaging target exists between the current imaging position and the previous imaging position, the user can return the ultrasound probe 50 in a direction opposite to the moving direction, and thus an observation target can be imaged at the imaging position for imaging.

Figure 12:
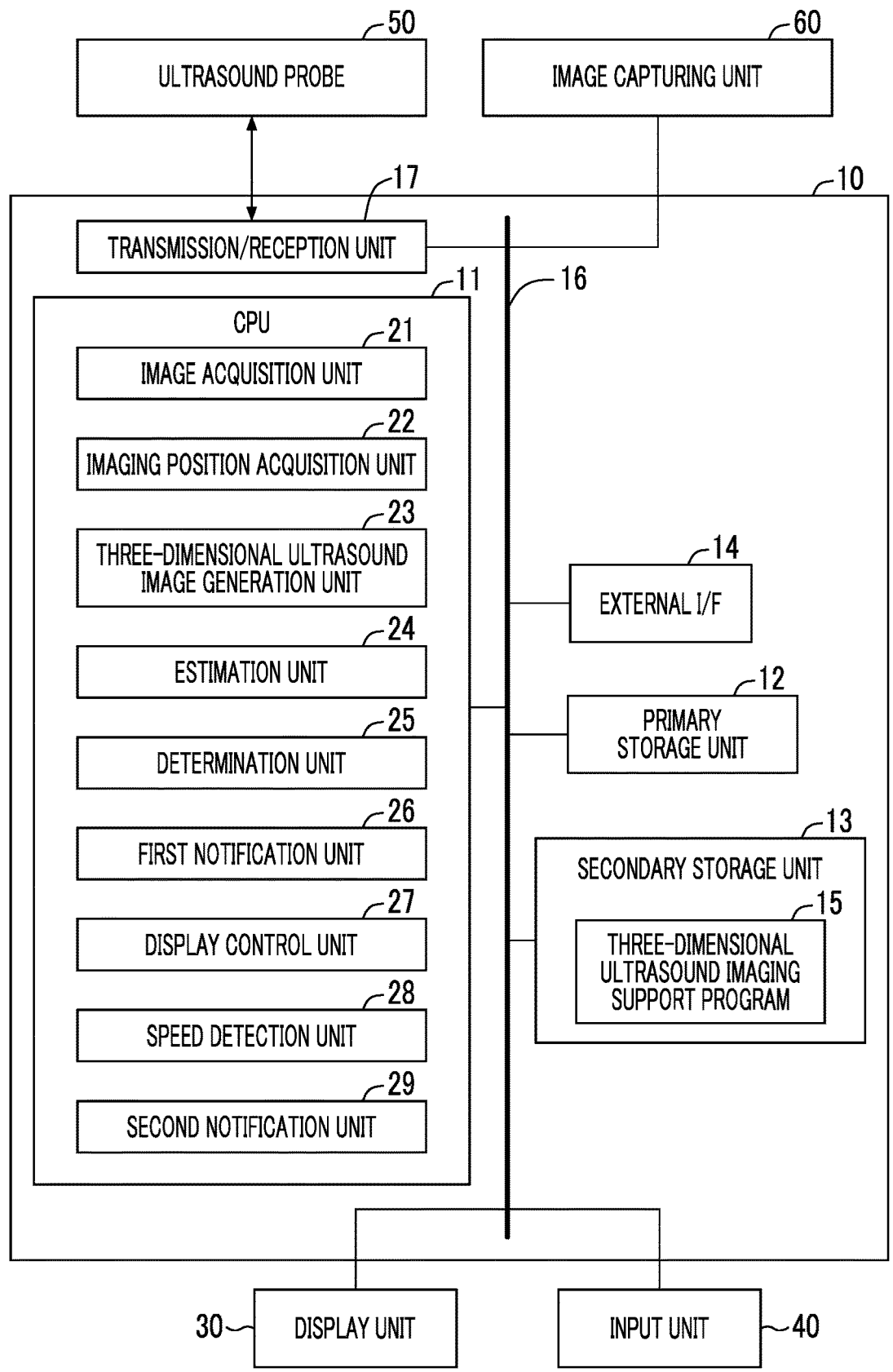
FIG. 12 is a schematic block diagram illustrating a configuration of a diagnosis support system including a three-dimensional ultrasound imaging support apparatus according to a third embodiment of the present disclosure.

Hereinafter, an embodiment of the present disclosure will be described with reference to the drawings. FIG. 12 is a schematic block diagram illustrating a configuration of a diagnosis support system to which a three-dimensional ultrasound imaging support apparatus according to a third embodiment is applied. In FIG. 12, the same reference numerals are given to the same configuration as the configuration of the diagnosis support system illustrated in FIG. 1. A description thereof will be omitted, and only different portions will be described.

As illustrated in FIG. 12, the three-dimensional ultrasound imaging support apparatus 10 according to the third embodiment includes a speed detection unit 28 and a second notification unit 29. The speed detection unit 28 detects whether or not the ultrasound probe 50 is moving at a predetermined speed based on the imaging position acquired by the imaging position acquisition unit 22. The imaging position acquisition unit 22 stores a time when the ultrasound probe 50 and the marker member 52 are captured by the image capturing unit 60, and detects a moving speed of the ultrasound probe 50 from a moving distance of the marker member 52 and the captured time.

In a case where the speed detection unit 28 detects that the ultrasound probe 50 is not moving at a predetermined speed, the second notification unit 29 performs notification indicating that the ultrasound probe 50 is not moving at a predetermined speed. As a notification method, for example, notification may be performed by sounding an alarm via a sound output unit (not illustrated), or the display unit 30 may display a message indicating "The ultrasound probe 50 is not moving at a predetermined speed". Thereby, it is possible to easily confirm whether or not the ultrasound probe 50 can be operated at a predetermined speed. Therefore, for example, a situation can be prevented where an observation target is not imaged at the imaging position for imaging because the speed is too fast.

In the present embodiment, in a case where the imaging portion is estimated by the estimation unit 24, the predetermined speed is predetermined for each estimated imaging portion. On the other hand, in a case where the imaging portion is not estimated by the estimation unit 24, a slowest speed among the speeds predetermined for all of the imaging portions is set as the predetermined speed.

Figure 13:
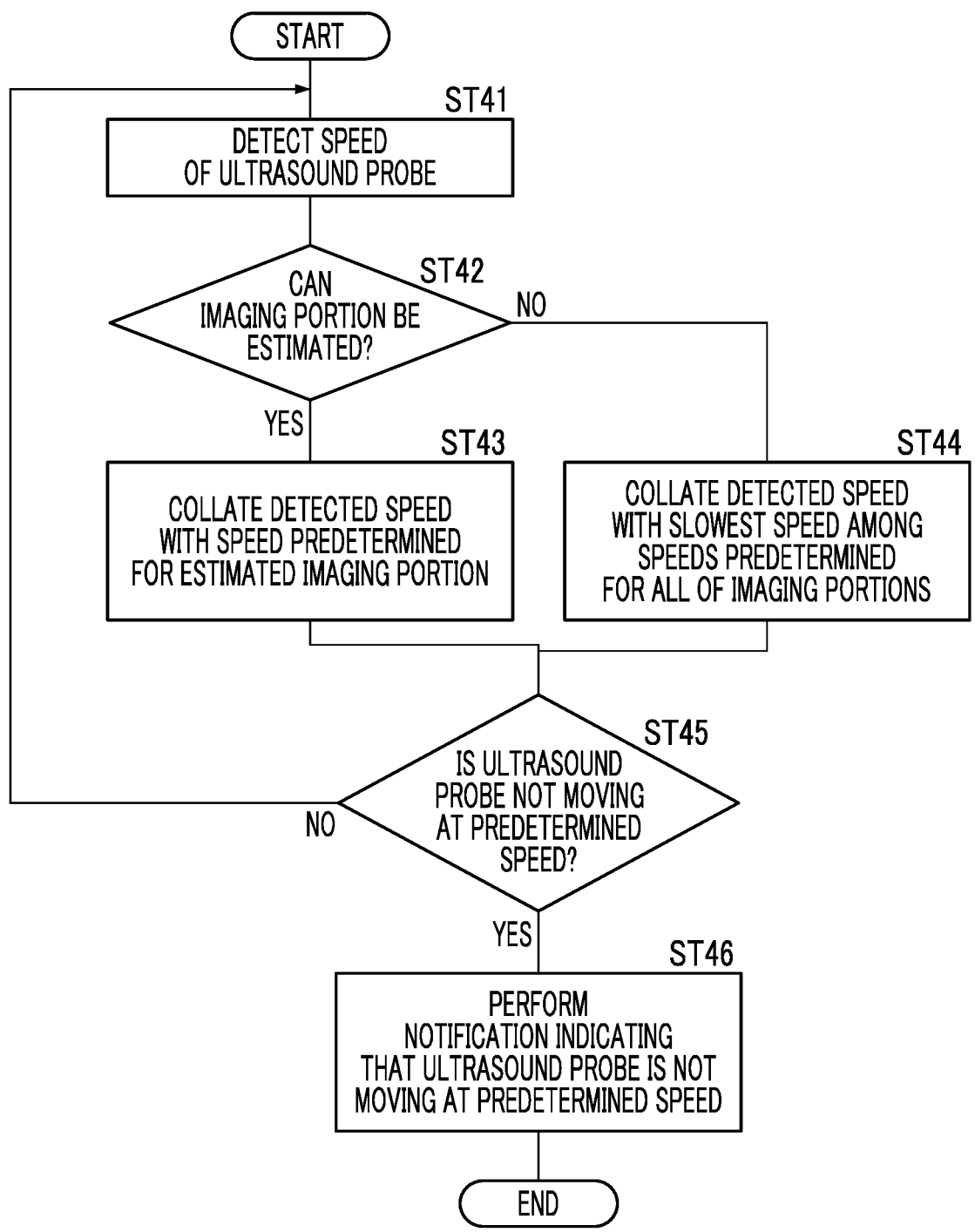
FIG. 13 is a flowchart illustrating processing performed in the third embodiment of the present disclosure.

Next, processing performed in the three-dimensional ultrasound imaging support apparatus according to the third embodiment will be described. FIG. 13 is a flowchart illustrating processing performed in the third embodiment of the present disclosure. The processing illustrated in FIG. 13 is performed in parallel with the processing according to the first embodiment illustrated in FIG. 9 and FIG. 10 or the processing according to the second embodiment illustrated in FIG. 11.

First, the speed detection unit 28 detects a speed of the ultrasound probe 50 (step ST41). At this time, the speed detection unit 28 determines whether or not the estimation unit 24 can estimate an imaging portion (step ST42). In a case where the imaging portion can be estimated, the speed detection unit 28 collates the detected speed with the speed defined in the guideline for the estimated imaging portion (step ST43).

On the other hand, in step ST42, in a case where the imaging portion cannot be estimated, the speed detection unit 28 collates the detected speed with a slowest speed among the speeds predetermined for all of the imaging portions (step ST44).

In a case where the speed detection unit 28 detects that the ultrasound probe 50 is not moving at a predetermined speed (YES in step ST45), the second notification unit 29 performs notification indicating that the ultrasound probe 50 is not moving at a predetermined speed (step ST46), and the processing is ended.

On the other hand, in step ST45, in a case where the speed detection unit 28 detects that the ultrasound probe 50 is moving at a predetermined speed (NO in step ST45), the CPU 11 transitions to processing of step ST41, and performs subsequent processing.

In the third embodiment, the user can recognize whether or not the ultrasound probe 50 can be operated at a predetermined speed for each imaging portion. Thereby, the user can move the ultrasound probe 50 at an appropriate speed for each imaging portion.

In the embodiments, the imaging position acquisition unit 22 derives information including the imaging position and the direction of the ultrasound probe 50, from the position of the marker center 52a, and the positions, the sizes, and the inclinations of the markers 52x, 52y, and 52z in the captured image acquired by capturing the ultrasound probe 50 and the marker member 52 by means of the image capturing unit 60. On the other hand, the technique of the present disclosure is not limited thereto.

The imaging position acquisition unit 22 may acquire information including the imaging position and the direction of the ultrasound probe 50 by using, for example, an augmented reality (AR) marker. The AR marker is an image including figures having a fixed pattern. The AR marker is provided on the outer circumferential surface of the ultrasound probe 50. By using a known program of detecting a position and a direction of the marker based on image data of the ultrasound probe 50 that includes the AR marker captured by the image capturing unit 60, the AR marker, that is, the information including the imaging position and the direction of the ultrasound probe 50, may be acquired.

Further, instead of the marker member 52, a projection portion and a recess portion may be provided on a main body of the ultrasound probe 50. In this case, information including the imaging position and the direction of the ultrasound probe 50 may be derived by using, as markers, the projection portion and the recess portion. In the technique of the present disclosure, the marker may have any shape and any form as long as the marker can be used as an index for defining the imaging position and the direction of the ultrasound probe 50, and is not particularly limited.

Further, for example, the diagnosis support system 1 may include a sensor instead of the image capturing unit 60 and the marker member 52.

Figure 14:
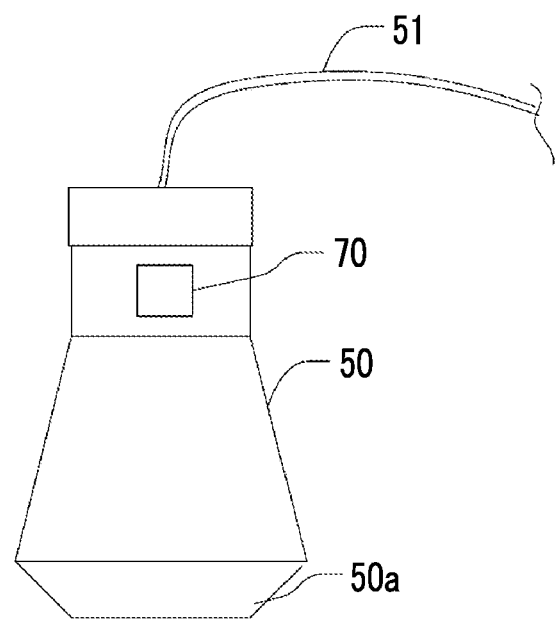
FIG. 14 is a diagram for explaining the ultrasound probe including a sensor.

FIG. 14 is a diagram for explaining the ultrasound probe including a sensor. In FIG. 14, attachment of a sensor to the ultrasound probe 50 is illustrated in a simple manner, unlike the actual shape.

As illustrated in FIG. 14, the ultrasound probe 50 includes a sensor 70 attached to the outer circumferential surface of the ultrasound probe 50. The sensor 70 is a six-axis sensor that can detect a moving direction, a direction, and a rotation and can further calculate a moving distance, a moving speed, and the like. The six-axis sensor is realized by combining an acceleration sensor that can detect three directions of a direction of front and back, a direction of right and left, and a direction of up and down with a geomagnetic sensor that can detect directions of north, south, east, and west, or by combining an acceleration sensor with a gyro sensor that can detect a speed of rotation.

The imaging position acquisition unit 22 can acquire the imaging position based on output information which is output from the sensor 70.

In the embodiment, the sensor 70 is provided instead of the image capturing unit 60 and the marker member 52. On the other hand, the technique of the present disclosure is not limited thereto. The sensor 70 may be provided, in addition to the image capturing unit 60 and the marker member 52. In this case, the sensor 70 is suitable for detecting the direction of the ultrasound probe 50, and a method of calculating the imaging position from the captured image acquired by capturing the ultrasound probe 50 and the marker member 52 by means of the image capturing unit 60 is suitable for detecting a parallel movement of the ultrasound probe 50. Thus, by using the image capturing unit 60, the marker member 52, and the sensor 70, the imaging position acquisition unit 22 can acquire the imaging position and the imaging direction with higher accuracy.

Further, in the above-described embodiment, for example, the following various processors may be used as a hardware structure of processing units performing various processing, such as the image acquisition unit 21, the imaging position acquisition unit 22, the three-dimensional ultrasound image generation unit 23, the estimation unit 24, the determination unit 25, the first notification unit 26, the display control unit 27, the speed detection unit 28, and the second notification unit 29. The various processors include, as described above, a CPU, which is a general-purpose processor that functions as various processing units by executing software (programs), and a dedicated electric circuit, which is a processor having a circuit configuration specifically designed to execute a specific processing, such as a programmable logic device (PLD) or an application specific integrated circuit (ASIC) that is a processor of which the circuit configuration may be changed after manufacturing such as a field programmable gate array (FPGA).

One processing unit may be configured by one of these various processors, or may be configured by a combination of two or more processors having the same type or different types (for example, a combination of a plurality of FPGAs or a combination of a CPU and an FPGA). Further, the plurality of processing units may be configured by one processor.

As an example in which the plurality of processing units are configured by one processor, firstly, as represented by a computer such as a client and a server, a form may be adopted in which one processor is configured by a combination of one or more CPUs and software and the processor functions as the plurality of processing units. Secondly, as represented by a system on chip (SoC) or the like, a form may be adopted in which a processor that realizes the function of the entire system including the plurality of processing units via one integrated circuit (IC) chip is used. As described above, the various processing units are configured by using one or more various processors as a hardware structure.

Further, as the hardware structure of the various processors, more specifically, an electric circuit (circuitry) in which circuit elements such as semiconductor elements are combined may be used.

EXPLANATION OF REFERENCES

1: diagnosis support system
10: three-dimensional ultrasound imaging support apparatus
11: CPU
12: primary storage unit
13: secondary storage unit
14: external I/F
15: three-dimensional ultrasound imaging support program
16: bus
17: transmission/reception unit
21: image acquisition unit
22: imaging position acquisition unit
23: three-dimensional ultrasound image generation unit
24: estimation unit
25: determination unit
26: first notification unit
27: display control unit
28: speed detection unit
29: second notification unit
30: display unit
40: input unit
50: ultrasound probe
60: image capturing unit
70: sensor

What is claimed is:
1. A three-dimensional ultrasound imaging support apparatus that supports imaging of an ultrasound image by a three-dimensional ultrasound apparatus for generating a three-dimensional ultrasound image, the apparatus comprising a processor, the processor configured to:
acquire a plurality of two-dimensional ultrasound images which are imaged by an ultrasound probe at different positions of a certain portion among a plurality of portions of a subject;
acquire an imaging position of the ultrasound probe for each imaging;
generate a three-dimensional ultrasound image based on the plurality of two-dimensional ultrasound images and the imaging position for each imaging;
estimate, from the plurality of portions of the subject, an imaging portion corresponding to the two-dimensional ultrasound image and to the three-dimensional ultrasound image, based on at least one of the two-dimensional ultrasound image or the three-dimensional ultrasound image;
determine, by using a guideline in which a plurality of imaging targets to be imaged are defined in advance for each of the portions of the subject, for the imaging portion, whether or not all of the plurality of imaging targets being defined in advance in the guideline are imaged in at least one of the plurality of two-dimensional ultrasound images or the three-dimensional ultrasound image; and
perform notification indicating that the imaging target which is not imaged is present in a case where the processor determines, for the imaging portion, that the imaging target which is not imaged is present among the plurality of imaging targets which are defined in advance in the guideline.

2. The three-dimensional ultrasound imaging support apparatus according to claim 1,
wherein, in a case where the processor determines, for the imaging portion, that the imaging target which is not imaged is present among the plurality of imaging targets which are defined in advance in the guideline,
the processor is configured to perform notification indicating the imaging position at which it is possible for the imaging target which is defined in the guideline and is not imaged to be imaged.

3. The three-dimensional ultrasound imaging support apparatus according to claim 2,
wherein the processor is configured to perform notification indicating the imaging position and a direction of the ultrasound probe at the imaging position.

4. The three-dimensional ultrasound imaging support apparatus according to claim 2, wherein
in a case where an imaging order of the plurality of imaging targets is defined in the guideline for each of the portions and the processor determines, by using the plurality of two-dimensional ultrasound images, whether or not all of the plurality of imaging targets which are defined in advance in the guideline are imaged,
the processor is configured to determine whether or not imaging is performed according to the imaging order which is defined in the guideline each time the two-dimensional ultrasound image is imaged, and
the processor is configured to perform notification according to a result of the determination.

5. The three-dimensional ultrasound imaging support apparatus according to claim 1, the processor is further configured to:
detect whether or not the ultrasound probe is moving at a predetermined speed based on the imaging position; and
perform notification indicating that the ultrasound probe is not moving at the predetermined speed in a case where the processor detects that the ultrasound probe is not moving at the predetermined speed.

6. The three-dimensional ultrasound imaging support apparatus according to claim 5,
wherein, in a case where the imaging portion is estimated, the processor detects whether or not the ultrasound probe is moving at a speed which is predetermined for the estimated imaging portion.

7. The three-dimensional ultrasound imaging support apparatus according to claim 1, further comprising:
a marker member that is fixed to the ultrasound probe; and
an image capturing unit that captures an image of the ultrasound probe and the marker member within the same image capturing range,
wherein the processor is configured to acquire the imaging position based on a captured image in which the ultrasound probe and the marker member are included and which is acquired by the image capturing unit.

8. The three-dimensional ultrasound imaging support apparatus according to claim 1, further comprising:
a six-axis sensor that is provided on the ultrasound probe,
wherein the processor is configured to acquire the imaging position based on output information which is output from the six-axis sensor.

9. The three-dimensional ultrasound imaging support apparatus according to claim 1, further comprising:
a marker member that is fixed to the ultrasound probe;
a six-axis sensor that is provided on the ultrasound probe; and
an image capturing unit that captures an image of the ultrasound probe and the marker member within the same image capturing range,
wherein the processor is configured to acquire the imaging position based on a captured image in which the ultrasound probe and the marker member are included and which is acquired by the image capturing unit and output information which is output from the six-axis sensor.

10. A three-dimensional ultrasound imaging support method that supports imaging of an ultrasound image by a three-dimensional ultrasound apparatus for generating a three-dimensional ultrasound image, the method comprising:
acquiring a plurality of two-dimensional ultrasound images which are imaged by an ultrasound probe at different positions of a certain portion among a plurality of portions of a subject;
acquiring an imaging position of the ultrasound probe for each imaging;
generating a three-dimensional ultrasound image based on the plurality of acquired two-dimensional ultrasound images and the acquired imaging position for each imaging;
estimating, from the plurality of portions of the subject, an imaging portion corresponding to the two-dimensional ultrasound image and to the three-dimensional ultrasound image, based on at least one of the acquired two-dimensional ultrasound image or the generated three-dimensional ultrasound image;
determining, by using a guideline in which a plurality of imaging targets to be imaged are defined in advance for each of the portions of the subject, for the imaging portion, whether or not all of the plurality of imaging targets being defined in advance in the guideline are imaged in at least one of the plurality of two-dimensional ultrasound images or the three-dimensional ultrasound image; and performing notification indicating that the imaging target which is not imaged is present in a case where it is determined that, for the imaging portion, the imaging target which is not imaged is present among the plurality of imaging targets which are defined in advance in the guideline.

11. A non-transitory computer readable recording medium storing a three-dimensional ultrasound imaging support program that supports imaging of an ultrasound image by a three-dimensional ultrasound apparatus for generating a three-dimensional ultrasound image, the program causing a computer to:

acquire a plurality of two-dimensional ultrasound images which are imaged by an ultrasound probe at different positions of a certain portion among a plurality of portions of a subject;

acquire an imaging position of the ultrasound probe for each imaging;

generate a three-dimensional ultrasound image based on the plurality of two-dimensional ultrasound images and the imaging position for each imaging;

estimate, from the plurality of portions of the subject, an imaging portion corresponding to the two-dimensional ultrasound image and to the three-dimensional ultrasound image, based on at least one of the two-dimensional ultrasound image or the three-dimensional ultrasound image;

determine, by using a guideline in which a plurality of imaging targets to be imaged are defined in advance for each of the portions of the subject, for the imaging portion, whether or not all of the plurality of imaging targets are imaged in at least one of the plurality of two-dimensional ultrasound images or the three-dimensional ultrasound image, the plurality of imaging targets being defined in advance in the guideline; and perform notification indicating that the imaging target which is not imaged is present in a case where the processor determines, for the imaging portion, that the imaging target which is not imaged is present among the plurality of imaging targets which are defined in advance in the guideline.

\* \* \* \* \*